United States Patent [19]

Brader

[11] Patent Number: 4,750,493
[45] Date of Patent: Jun. 14, 1988

[54] METHOD OF PREVENTING BRAIN DAMAGE DURING CARDIAC ARREST, CPR OR SEVERE SHOCK

[76] Inventor: Eric W. Brader, 3211 Nottingham Rd., Pittsburgh, Pa. 15235

[21] Appl. No.: 834,341

[22] Filed: Feb. 28, 1986

[51] Int. Cl.[4] .............................................. A61F 7/10
[52] U.S. Cl. ........................................ 128/380; 62/4; 128/402
[58] Field of Search ............... 128/380, 399, 402, 403; 62/4

[56] References Cited

U.S. PATENT DOCUMENTS

| | | | |
|---|---|---|---|
| 683,991 | 10/1901 | Rowe | 128/402 |
| 4,382,446 | 5/1983 | Truelock et al. | 128/402 |

OTHER PUBLICATIONS

"Current Medical Diagnosis and Treatment", copyright 1985, publ. by Lange Medical Publications, Los Altos, Calif., p. 10.
Profound Hypothermia: Value of Prolonged Cardiopulmonary Resuscitation, South Med. J., 1981, 74: 474–477.
Neurological Recovery After Cardiac Arrest: Effect of Duration of Ischemia, Crit. Care Med. 1985, 13:11, 930–931.

Primary Examiner—Anton O. Oechsle
Attorney, Agent, or Firm—Webb, Burden, Robinson & Webb

[57] ABSTRACT

A method for cooling the extracranial area including the face and, optionally, also including the mandible, during emergency care of cardiac arrest or severe shock; the method is preferably implemented by means of a hood- or cap-like topical cold pack which requires no refrigeration. Extracranial cooling causes two thermal changes in the physiology of the cardiac or respiratory patient: extracranial vasoconstriction promotes maximum perfusion to the brain during CPR or severe shock, and the resultant conductive intracranial cooling lowers the oxygen demands of the individual brain cells, particularly those of the cerebrum. These two phenomena together postpone damage to brain cells in the event of cardiac arrest or severe shock. Cooling also thermodynamically slows any degenerative processes which may have already commenced. The hood- or cap-like topical cold pack contains the unreacted constituents of an endothermic reaction, such as pellets of ammonium nitrate ($NH_4NO_3$) stored adjacent a selectively available reservoir of water, and thus needs no external refrigeration, coolant or insulation for storage. The topical cold pack is thus well suited for use in emergency care settings for which refrigeration may not be available.

2 Claims, No Drawings

METHOD OF PREVENTING BRAIN DAMAGE DURING CARDIAC ARREST, CPR OR SEVERE SHOCK

FIELD OF THE INVENTION

The present invention is a method of inhibiting tissue metabolism in the area of the brain and, more particularly, is a method inducing localized hypothermia during the emergency treatment of cardiac arrest or severe shock.

BACKGROUND OF THE INVENTION

Systemic hypothermia can dramatically postpone neurologic deterioration in hypoxic or anoxic tissues. For example, accidental submersion in cold waters, and the commensurate systemic hypothermia thus produced, has consistently contributed to the neurologic survival of accident victims who would have otherwise sustained irreparable brain damage. Observation of this phenomenon led medical practitioners to induce, intentionally, systemic hypothermia in the course of various hypoxia- and anoxia-producing surgical procedures, in order to decrease both the systemic metabolism and the associated overall oxygen requirement of the patient.

Whereas systemic hypothermia may be induced without difficulty in the hospital environment, emergency inducement of systemic hypothermia in a non-hospital setting can be difficult or impossible. As a result, induced systemic hypothermia forms no part of, for example, pre-hospital emergency cardiac care such as cardiopulmonary resuscitation (CPR), notwithstanding the beneficial metabolic inhibition which such hypothermia would provide. Similar emergency procedures in which hypothermia has not been induced to date include the pre-hospital emergency care administered to patients in severe shock.

SUMMARY OF THE PRIOR ART

Induced localized hypothermia has been used widely in the non- or pre-hospital treatment of numerous physiologic conditions. Cold packs of some sort are standard equipment in first aid kits, and are used to decrease peripheral blood flow (and commensurate swelling) in the event of contusion, insect bites or stings, nosebleeds, sprains, etc. Cold compresses to the head, of course, have long been a standard symptom-relieving measure for headaches and fever. In addition to these common treatments, however, three of the less well-known uses for topical cold applications are described in U.S. Pat. Nos. 2,438,643, No. 3,175,558 and No. 4,552,149.

U.S. Pat. No. 2,438,643 discloses a pack, for use in local refrigeration anesthesia, which contains a plurality of waterproof compartments which contain brine and an absorbent material, such as sawdust. The pack may be cooled in any suitable refrigerating device and then used as a topical cold pack. Because the pack must be refrigerated, its utility for inducing localized hypothermia is limited to those areas for which refrigeration is available.

U.S. Pat. No. 4,552,149 also discloses a coolant-containing, refrigerant-dependent cold pack which is, more specifically, a head coolant device. The device comprises a main body consisting of a cooling piece for covering the top of the head and a plurality of cooling pieces radially arranged around the main body, for covering the front, sides and back of the head. This head cooling cap is designed to inhibit hair loss during the administration of a drug or chemotherapeutic agent for which hair loss is a known side effect. As with all cold packs which require refrigeration, the head coolant device is best suited to hospital and home application, and is not well suited for use in the types of pre-hospital emergency care for which refrigeration may be unavailable.

U.S. Pat. No. 3,175,558 discloses a thermal therapeutic pack, specifically designed for postpartum application to the female perineum, which contains the unreacted constituents of an endothermic reaction. (Similar heat packs may contain the unreacted constituents of an exothermic reaction.) The unreacted constituents are separated by frangible barriers, time-release capsules, or both, and the separation is maintained until the cold pack is needed. At the time of use, the reactants are admixed (by, for example, manually cracking the frangible barrier between them), the endothermic reaction renders the entire cold pack "cold," and the pack is positioned on the patient, as required, to cool the area of application by the reverse conductive heating of the pack by the body.

Accordingly, the prior art devices do not provide for, and the existing medical emergency treatments do not accommodate, the inducing of hypothermia (either systemic or localized) in the emergency treatment of cardiac arrest or severe shock. A need therefore remains for a method of inducing sufficient hypothermia in the cardiac arrest or severe shock patient, and an apparatus for accomplishing it, to increase the chances for successful resuscitation unaccompanied by neurologic loss.

BRIEF DESCRIPTION OF THE INVENTION

In order to meet this need, the present invention is a method for cooling the extracranial area including the face and, optionally, also including the mandible, during emergency care of cardiac arrest or severe shock; the method is preferably implemented by means of a hood- or cap-like topical cold pack which requires no refrigeration. Extracranial cooling causes two thermal changes in the physiology of the cardiac or respiratory patient: extracranial vasoconstriction promotes maximum perfusion to the brain during CPR or severe shock; and the resultant conductive intracranial cooling lowers the oxygen demands of the individual brain cells, particularly those of the cerebrum. These two phenomena together postpone damage to brain cells in the event of cardiac arrest or severe shock. If degenerative processes have begun, cooling will thermodynamically slow them. The hood- or cap-like topical cold pack contains the unreacted constituents of an endothermic reaction, such as pellets of ammonium nitrate ($NH_4NO_3$) stored adjacent a selectively available reservoir of water, and thus needs no external refrigeration, coolant or insulation for storage. The topical cold pack is thus well suited for use in emergency care settings for which refrigeration may not be available.

DETAILED DESCRIPTION OF THE INVENTION

The present method for preventing brain damage during cardiac arrest or severe shock comprises inducing localized hypothermia in the extracranial area including the face, and optionally also including the mandible, in order to precipitate both extracranial vasoconstriction and intracranial cooling by conduction. This method of cooling the external area of the cranium without likewise cooling, for example, the torso and extremities, is moreover physiologically preferable to the more drastic induction of systemic hypothermia. In theory, although Applicant does not wish to be bound by this theory, the localized cranial cooling simplifies rewarming and minimizes "afterdrop," the continued decrease in body temperature which occurs after topical cooling means are removed. In addition, cranial cooling is preferred to systemic cooling for its obvious convenience in both in-hospital and pre-hospital patient care.

Applicant surmises an explanation, which follows, of the physiologic effects of extracranial cooling which result in neurologic preservation. Applicant does not wish to be bound by this explanation, however, because it is his method and the structure, function and result of his apparatus which constitute the present invention, not the elements of his theory.

In circulatory arrest, brain oxygen stores are exhausted within 10 seconds. (Commensurate oxygen deficiency accompanies severe shock.) Subsequent to brain anoxia, anaerobic glycolysis proceeds for approximately 4 minutes with concomitant buildup of lactic acid and exhaustion of glucose stores. Energy production thereafter ceases, causing the sodium-potassium ATPase pump to fail at the brain cell membrane. Consequent depolarization of the cell membrane permits massive calcium influx, which is thought to trigger the pathophysiology which leads to postischemic encephalopathy (PIE). Return of spontaneous circulation (ROSC), with its accompanying massive calcium sequestration from the cells, probably also contributes to intoxication of both mitochondria and smooth endoplasmic reticula, along with the formation of free radicals catalyzed by delocalized low molecular weight iron. Other aspects of pathophysiology include hypermetabolism, vasoparalysis, loss of blood-brain barrier integrity and coagulopathy.

By cooling the head, extracranial vasoconstriction increases cerebral blood flow at the same time as intracranial hypothermia retards both ATP depletion in the brain cells and subsequent membrane depolarization by thermodynamically decreasing metabolic demand. CPR-generated cerebral blood flow, maximized due to extracranial vasoconstriction, may be adequate to meet this reduced metabolic demand. If not, however, and in the event that brain cell membrane failure (depolarization) occurs despite head cooling, the hypothermia also thermodynamically inhibits the degenerative processes associated with cell membrane failure. Upon ROSC, reperfusion injury is likewise thermodynamically blunted.

In addition, because much of the ischemia-sensitive cerebral tissue is located peripherally within the cranium and is poorly insulated from the environmental temperature, Applicant believes that surface cooling of the head quickly provides therapeutic levels of hypothermia in those very areas of the brain which are most sensitive to ischemia, in addition to providing almost immediate extracranial vasoconstriction.

Although any extracranial cooling is beneficial during respiratory or cardiac insufficiency, profound head cooling is preferred. Profound head cooling is particularly preferred during cardiac or respiratory arrest, for which resuscitation time is otherwise drastically limited. (Frostbite avoidance and skin temperature monitoring may be carried out by means known in the art although, of course, frostbite is always preferable to neurologic loss.) As is impossible with induced systemic hypothermia, however, even profound cranial hypothermia is clinically feasible, due to the buffering of the cold venous return from the head by the warm venous return from the body. Apparently this buffering of cold venous return from the head is responsible for minimizing both unwanted afterdrop and undesirable myocardial and pulmonary cooling during treatment of the patient.

Although the method of cooling the exterior of the cranium, including the face and optionally the mandible, may be accomplished by a number of means, including both conductive and convective means such as conventional ice packs and the like, the preferred apparatus as claimed herein is a hood- or cap-like topical cold pack which functions as a head cooling apparatus without need for external refrigeration. Structurally, the topical cold pack may have any configuration which permits topical application to the extracranial area including the face, and may additionally have a means for topical application to the mandible. Accordingly, the topical cold pack may be a hood or a cap, or a wrap or sheet suitable for wrapping into a face-covering hood- or cap-like configuration.

The claimed apparatus, in order to free it from the need for external refrigeration, contains the unreacted constituents of an endothermic reaction, such as pellets of ammonium nitrate ($NH_4NO_3$) stored adjacent a selectively available reservoir of water. These endothermic reactants are known in the art, as are the means for separating the reactants until the cold pack is needed. The present claimed apparatus differs from known cold packs, however, in that in all cases the topical cold pack is designed to cover the face as well as the top, back and sides of the head. Cooling of the face is essential to the present invention because normothermic extracranial perfusion to the face accounts for a significant portion of total extracranial perfusion, and maximum cerebral blood flow thus requires cooling of the entire extracranial area *including* the face. By the term "face," Applicant signifies the cartilaginous and soft tissues adjacent to and covering the anterior cranium proper; the tissues which cover the mandible need only optionally be cooled because extracranial facial perfusion concentrates in the general area of the eyes and nose.

Although the present method and apparatus have broad application in the emergency treatment of humans, the utility of the present method and apparatus has thus far been documented in canine studies in the laboratory. Accordingly, the following examples are illustrative not only of the present claimed method but of the efficacy of the results obtained to date.

EXAMPLE I

Twelve healthy flat-chested 12-25 kg. mongrel dogs fasted, although water was permitted, overnight. The dogs were premedicated with 10 mg./kg. body weight ketamine and were subsequently anesthetized with a gaseous admixture of nitrous oxide, oxygen and halothane. Endotrachial intubation was performed when anesthesia reached sufficient depth. Pre-insult temperature was maintained between 37°-38° C. Supradiaphragmatic aortic and Swan Ganz catheters were placed via femoral cutdown. The head of each dog was shaved.

After the level of anesthesia was allowed to lighten, by allowing all dogs to breathe room air spontaneously for 4–6 minutes, ventricular fibrillation was introduced transthoracically with 100V AC. Upon confirmation of ventricular fibrillation, six dogs had their heads cooled. This was achieved by first wetting and then packing each head in ice bags. The chest of each animal was stabilized with sandbags.

Each dog was subjected to 4 minutes of ventricular fibrillation and 20 minutes of "controlled" CPR, during which sixty A-P compressions per minute were delivered by a Michigan Instruments Thumper, and one ventilation (25 cc./kg., $FIO_2 = 1.0$) was administered after every fifth compression. When initial systolic blood pressure read below 40 mm Hg, the animal was excluded from consideration. No increases in pressure of chest compression were allowed after 5 minutes of CPR.

Restoration of spontaneous circulation was then attempted by means known in the art. Rewarming was achieved by heating pads applied to the body but not the head. Median arterial pressure was maintained above 80 mm Hg using a continuous epinephrine infusion and fluid administration titrated by pulmonary artery pressors. Weaning from mechanical ventilation was begun one hour after restoration of spontaneous circulation. All dogs received 4–5 hours of intensive care, and were then returned to their cages with supplemental oxygen and maintenance IV's.

EXAMPLE II

For dogs treated as in Example I, neurologic deficit scores (NDS) were obtained at 3, 12 and 24 hours post-resuscitation. These NDS values were assigned according to the following guidelines.

|  | Points Assigned | | Scores | |
| --- | --- | --- | --- | --- |
|  | Best | Worst | Best | Worst |
| Level of consciousness | 0 | 100 | 0 | 20 |
| Respiration | 0 | 100 | 0 | 20 |
| Cranial nerve functon | 0 | 100 | 0 | 20 |
| Motor and sensory function | 0 | 100 | 0 | 20 |
| Behavior | 0 | 100 | 0 | 20 |
| TOTAL | 0 | 500 | 0 | 100% |

| -continued | |
| --- | --- |
| Fully awake. Can sit, feed self, stand. May have moderate motor deficit or ataxia. | 0–15% |
| Fully awake. More severe motor deficit Cannot sit, stand, feed self. Eats when fed. Dog can right itself and stay in position. | 15–25% |
| Not awake - difficult to arouse. Some awareness off/on. Can move all limbs, but spastic. Reacts to pain. Cannot sit, stand or eat. Dog able to keep head up. Can stay in righting position, but cannot right self. Dog's position normal or a tendency for flexation with some running movements on or off. | 25–40% |
| No awareness. Often abnormal body position. Spontaneous extension of extremities. Vegetative, spontaneous running movements often with opistotonus. May exbibit spinal cord hyperreflex-activity. Vision may be severely impaired. | 40–80% |
| Totally unresponsive. Brain death or dying a cerebral death during the observation period. | 80–100% |

The head-cooled dogs had significantly better neurological outcomes than did the normothermic control dogs. Mean NDS, for the head-cooled dogs not excluded from consideration (exclusions were made for reasons well established in experimental surgical neurology), estimated at 3 hours post-ROSC, was 37.2%, whereas mean NDS for control dogs was 61.8%. Furthermore, although 2 head-cooled dogs survived 24 hours (one neurologically intact and one having an NDS of only 9%), none of the control dogs survived 24 hours.

Although the invention has been described with reference to specific materials and specific processes, the invention is to be limited only insofar as is set forth in the accompanying claims.

I claim:

1. A method for treating a human being, during cardiac arrest or severe shock, comprising cooling the extracranial tissues, including the tissues of the face, to initiate both extracranial vasoconstriction and intracranial hypothermia, thereby increasing cerebral blood flow to and decreasing the oxygen requirements of the brain.

2. The method according to claim 1, further comprising cooling the tissues adjacent the mandible.

* * * * *